United States Patent
Hung et al.

(10) Patent No.: US 9,321,993 B2
(45) Date of Patent: Apr. 26, 2016

(54) TISSUE CULTURE METHOD FOR PRODUCING CARTILAGE USING TRIMETHYLAMINE N-OXIDE AND CHONDROITINASE

(75) Inventors: Clark T. Hung, Ardsley, NY (US); Grace D. O'Connell, Lansdowne, PA (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 13/704,839

(22) PCT Filed: Jun. 17, 2011

(86) PCT No.: PCT/US2011/040875
§ 371 (c)(1),
(2), (4) Date: Feb. 27, 2013

(87) PCT Pub. No.: WO2011/160012
PCT Pub. Date: Dec. 22, 2011

(65) Prior Publication Data
US 2013/0202567 A1    Aug. 8, 2013

Related U.S. Application Data

(60) Provisional application No. 61/355,915, filed on Jun. 17, 2010, provisional application No. 61/379,667, filed on Sep. 2, 2010.

(51) Int. Cl.
*C12N 5/00*        (2006.01)
*C12N 5/077*       (2010.01)
*A61K 35/32*       (2015.01)

(52) U.S. Cl.
CPC .............. *C12N 5/0655* (2013.01); *A61K 35/32* (2013.01); *C12N 2500/46* (2013.01); *C12N 2500/60* (2013.01); *C12N 2501/115* (2013.01); *C12N 2501/135* (2013.01); *C12N 2501/15* (2013.01); *C12N 2501/73* (2013.01); *C12N 2533/76* (2013.01)

(58) Field of Classification Search
None
See application file for complete search history.

(56) References Cited

U.S. PATENT DOCUMENTS 5,916,557 A * 6/1999 Berlowitz-Tarrant et al. ............... 424/94.5
6,110,504 A   8/2000 Segall et al.
2002/0041900 A1 * 4/2002 Olsen et al. ............ 424/538

FOREIGN PATENT DOCUMENTS

WO  WO 2004/043401 A2  5/2004
WO  WO 2005/007098 A2  1/2005

OTHER PUBLICATIONS

Bian et al., Influence of Temporary Chondroitinase ABC-Induced Glycosaminoglycan Suppression on Maturation of Tissue-Engineered Cartilage, Tissue Engineering: Part A, 2009, pp. 2065-2072, vol. 15, No. 8.
Dillon et al., RNAi as an Experimental and Therapeutic Tool to Study and Regulate Physiological and Disease Processes, Annu. Rev. Physiol., 2005, pp. 147-173, vol. 67.
Dykxhoorn et al., The Silent Revolution: RNA Interference as Basic Biology, Research Tool, and Therapeutic, Annu. Rev. Med., 2005, pp. 401-423, vol. 56.
Elhai et al., Conjugal Transfer of DNA to Cyanobacteria, Methods in Enzymology, 1988, pp. 747-754, vol. 167.
Helene et al., Control of Gene Expression by Triple Helix-Forming Oligonucleotides, Ann. NY Acad Sci., 1992, pp. 27-36, vol. 660.
International Search Report and Written Opinion dated Nov. 16, 2011 in corresponding International Application No. PCT/US2011/040875, 7 pages.
Lee et al., Aptamer therapeutics advance, Curr. Opinion Chem. Biol., 2006, pp. 282-289, vol. 10.
Maher, DNA Triple-Helix Formation: An Approach to Artificial Gene Repressors?, BioEssays, 1992, pp. 807-815, vol. 14, No. 12.
Meersman et al., Counteraction of Urea by Trimethylamine N-Oxide is Due to Direct Interaction, Biophysical Journal, 2009, pp. 2559-2566, vol. 97.
Pushparaj et al., Short Interfering RNA (siRNA) as a Novel Therapeutic, Clinical and.Experimental Pharmacology and Physiol., 2006, pp. 504-510, vol. 33.
Reynolds et al., Rational siRNA design for RNA interference, Nature Biotechnology, 2004, pp. 326-330, vol. 22, No. 3.
Yancey, Organic osmolytes as compatible, metabolic and counteracting cytoprotectants in high osmolarity and other stresses, J. Experimental Biology, 2005, pp. 2819-2830, vol. 208.
Glowacki, In Vitro Engineering Cartilage, Journal of Rehabilitation Research & Development, vol. 37, No. 2, Mar./Apr. 2000, pp. 171-178.
Hartmann et al., Letter to the Editor—Routine Establishment of Primary Elasmobranch Cell Cultures, In Vitro Cell. Dev. Biol., vol. 28A, Feb. 1992, pp. 77-79.
Martin, Maintaining The Internal Sea, downloaded Dec. 30, 2015 from the internet at http://www.elasmo-research.org/education/white_shark/tmao.htm (2 pages).
Zou et al., The Molecular Mechanism of Stabilization of Proteins by TMAO and Its Ability to Counteract the Effects of Urea, J. Am. Chem. Soc., vol. 124, No. 7, 2002, pp. 1192-1202.

* cited by examiner

*Primary Examiner* — Blaine Lankford
(74) *Attorney, Agent, or Firm* — Dentons US LLP

(57) ABSTRACT

The present disclosure provides cell culture medium comprising trimethylamine N-oxide (TMAO). Progenitor cells cultured with such medium can form connective tissue with enhanced mechanical properties. Also provided are methods of forming connective tissue and methods of treatment for connective tissue defects.

18 Claims, 9 Drawing Sheets

TISSUE CULTURE METHOD FOR PRODUCING CARTILAGE USING TRIMETHYLAMINE N-OXIDE AND CHONDROITINASE

CROSS-REFERENCE TO RELATED APPLICATIONS

The present application claims the benefit of priority to PCT International Application No. PCT/US11/40875 filed 17 Jun. 2010, which claims the benefit of U.S. Provisional Application Ser. No. 61/355,915, filed on 17 Jun. 2010, and U.S. Provisional Application Ser. No. 61/379,667, filed on 2 Sep. 2010, each of which is incorporated herein by reference in its entirety.

STATEMENT REGARDING FEDERALLY SPONSORED RESEARCH OR DEVELOPMENT

Not Applicable.

MATERIAL INCORPORATED-BY-REFERENCE

Not Applicable.

FIELD OF THE INVENTION

The present invention generally relates to tissue culture, specifically culture media supplements for altering properties of cultured tissue.

BACKGROUND

Trimethylamine N-oxide (TMAO), also known by several other names and acronyms, is an organic compound with the formula $(CH_3)_3NO$. This colorless solid is usually encountered as a dihydrate. It is an oxidation product of trimethylamine and a common metabolite in animals. It is an osmolyte found in saltwater fish, sharks and rays, molluscs, and crustaceans. Along with free amino acids, it reduces the 3% salinity of seawater to about 1% of dissolved solids inside cells. TMAO decomposes to trimethylamine (TMA), which is the main odorant that is characteristic of degrading seafood. TMAO is thought to counteract the effects of urea by stabilizing protein folding in shark tissue (see Yancey 2005 J Exp Biol 208(Pt 15), p. 2819-2830; Meersman et al. 2009 Biophys J 97(9), 2559-2566).

There are enormous differences between sharks and other fish. In particular, unlike other vertebrates, sharks have a skeletal structure of cartilage instead of bone. Urea and trimethylamine in their blood and tissues help to maintain their osmotic balance. Like other sharks, the Great White's bodily fluids also contain small organic molecules. Among the most important of these from an osmotic standpoint are urea and TMAO. Both urea and TMAO are nitrogen-containing breakdown products of protein metabolism. Urea is highly toxic to living tissue at moderate to high concentrations, causing proteins to de-stabilize and thus cease to function properly or at all. That is why, although a body can retain urea for a short time, it must be eventually excreted or dire physiological consequences occur. Yet sharks routinely retain bodily concentrations of urea that would kill most other vertebrates. This is largely due to the presence of even higher bodily concentrations of TMAO, which counters the protein-de-stabilizing effects of urea. Together, urea and TMAO add substantially to a shark's osmotic pressure, effectively rendering the internal fluids slightly (about 5%) "saltier" than the external environment. As a result, sharks do not need to invest any additional metabolic effort toward obtaining the water their bodies need. A constant supply of fresh water osmoses passively into a shark's body through the gills and other exposed membranes.

SUMMARY OF THE INVENTION

One aspect provides a chondrogenic tissue culture medium comprising trimethylamine N-oxide (TMAO). In some embodiments, the medium can include about 10 mM, about 20 mM, about 30 mM, about 40 mM, about 50 mM, about 60 mM, about 70 mM, about 80 mM, about 90 mM, about 100 mM, about 110 mM, about 120 mM, about 130 mM, about 140 mM, about 150 mM, about 160 mM, about 170 mM, about 180 mM, about 190 mM, about 200 mM, about 250 mM, about 300 mM, about 400 mM, about 450 mM, about 500 mM, about 550 mM, about 600 mM, about 650 mM, about 700 mM, about 750 mM, about 800 mM, about 850 mM, about 900 mM, about 950 mM, or about 1,000 mM TMAO.

In some embodiments, the medium comprises urea. In some embodiments, the medium can include about 10 mM, about 20 mM, about 30 mM, about 40 mM, about 50 mM, about 60 mM, about 70 mM, about 80 mM, about 90 mM, about 100 mM, about 110 mM, about 120 mM, about 130 mM, about 140 mM, about 150 mM, about 160 mM, about 170 mM, about 180 mM, about 190 mM, about 200 mM, about 250 mM, about 300 mM, about 400 mM, about 450 mM, about 500 mM, about 550 mM, about 600 mM, about 650 mM, about 700 mM, about 750 mM, about 800 mM, about 850 mM, about 900 mM, about 950 mM, or about 1,000 mM urea.

In some embodiments, medium includes TMAO and urea at a ratio (TMAO:urea) of about 100:1, about 90:1, about :1, about 80:1, about 70:1, about 60:1, about 50:1, about 40:1, about 30:1, about 20:1, about 10:1, about 9:1, about 8:1, about 7:1, about 6:1, about 5:1, about 4:1, about 3:1, about 2:1, about 1:1, about 1:2, about 1:3, about 1:4, about 1:5, about 1:6, about 1:7, about 1:8, about 1:9, about 1:10, about 1:20, about 1:30, about 1:40, about 1:50, about 1:60, about 1:70, about 1:80, about 1:90, or about 1:100.

In some embodiments, medium includes chondroitinase (cABC). In some embodiments, the medium can include at least about 0.01 U/mL, at least about 0.02 U/mL, at least about 0.03 U/mL, at least about 0.04 U/mL, at least about 0.05 U/mL, at least about 0.06 U/mL, at least about 0.07 U/mL, at least about 0.08 U/mL, at least about 0.09/mL, at least about 0.10 U/mL, at least about 0.11 U/mL, at least about 0.12/mL, at least about 0.13 U/mL, at least about 0.14 U/mL, at least about 0.15 U/mL, at least about 0.16 U/mL, at least about 0.17 U/mL, at least about 0.18 U/mL, at least about 0.19 U/mL, at least about 0.20 U/mL, at least about 0.25 U/mL, at least about 0.30 U/mL, at least about 0.40 U/mL, at least about 0.50 U/mL, at least about 0.60 U/mL, at least about 0.70 U/mL, at least about 0.80 U/mL, at least about 0.90 U/mL, at least about 1.0 U/mL, at least about 1.1 U/mL, at least about 1.2 U/mL, at least about 1.3 U/mL, at least about 1.4 U/mL, or at least about 1.5 U/mL cABC.

In some embodiments, medium includes Dulbecco's Modified Eagle Medium (DMEM). In some embodiments, medium includes one or more of: dexamethasone, proline, ascorbate 2-phosphate, sodium pyruvate, insulin, transferrin, sodium selenite, penicillin, streptomycin amphotericin, or TGF-$\beta_3$.

Another aspect is a method for producing cartilage tissue. In some embodiments, the method includes culturing chondrogenic progenitor cells in a culture medium containing TMAO. In some embodiments, the method includes digesting cultured chondrogenic progenitor cells with chondroitinase. In some embodiments, the method includes contacting cultured chondrogenic progenitor cells with a culture medium described above.

In some embodiments, the method produces a connective tissue, such as cartilage. In some configurations, the methods produces cartilage tissue having increased stiffness compared to cartilage tissue not cultured in the presence of TMAO.

In some embodiments, the method includes introducing the chondrogenic progenitor cell into or onto a biocompatible matrix. Introduction can be before or after exposure to TMAO.

Another aspect provides a method of treating a connective tissue defect in a subject. In some embodiments, the method includes culturing chondrogenic progenitor cells in a culture medium containing TMAO and introducing the cultured cells into a subject in need thereof.

Other objects and features will be in part apparent and in part pointed out hereinafter.

BRIEF DESCRIPTION OF THE DRAWINGS

Those of skill in the art will understand that the drawings, described below, are for illustrative purposes only. The drawings are not intended to limit the scope of the present teachings in any way.

In FIG. 6A, GAG content was normalized to wet weight at day 42 In FIG. 6B, OHP content was normalized to the wet weight at day 28. *$p<0.05$ vs. control using a two-way ANOVA and a Bonferonni post hoc test. Further details regarding methodology are provided in Example 3.

DETAILED DESCRIPTION OF THE INVENTION

Figure 1:
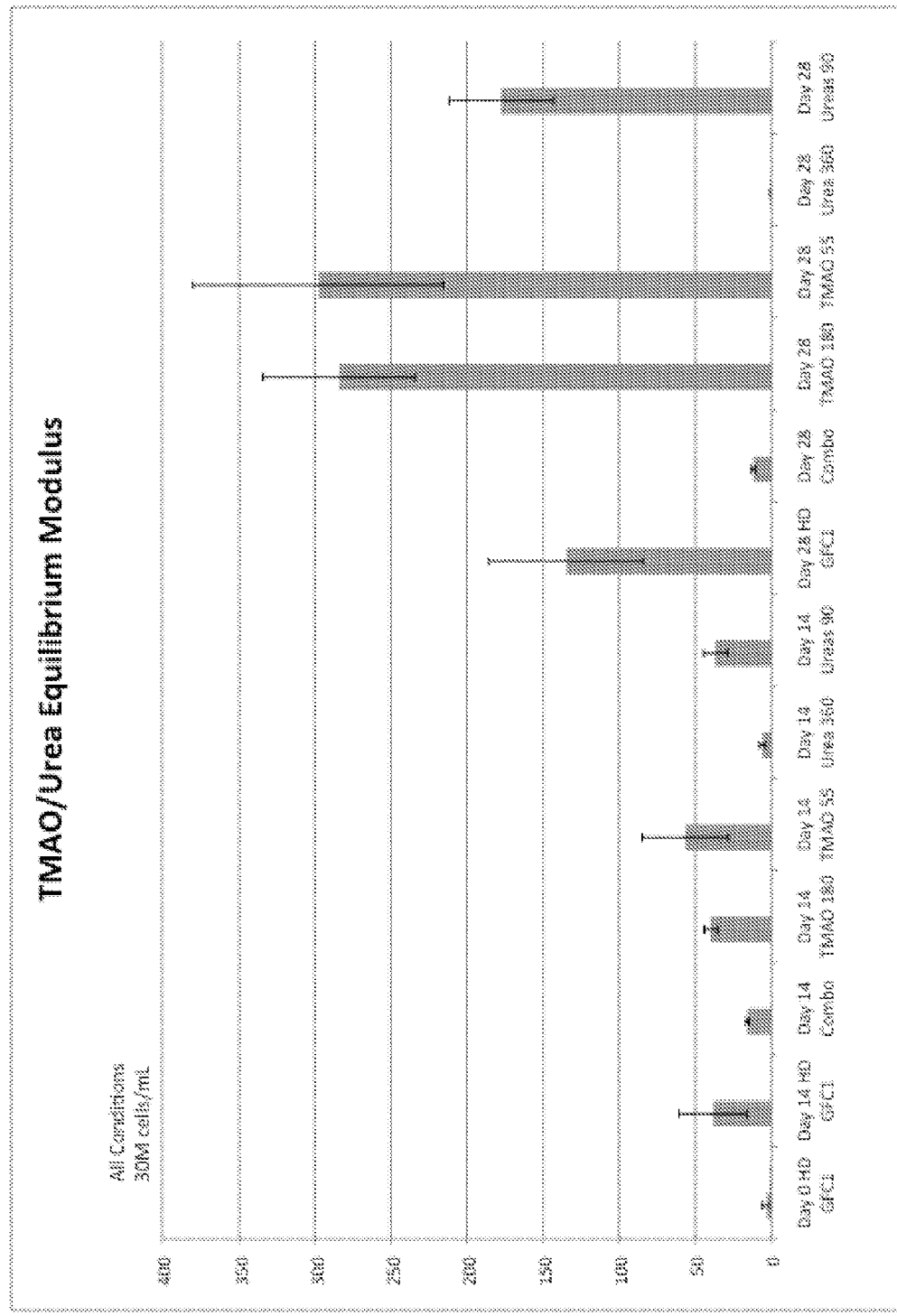
FIG. 1 is a bar graph showing Young's modulus, a measure of mechanical stiffness, of tissue (30M cells/mL) cultured with TMAO (180 or 55 mM), urea (360 or 90 mM), or TMAO_urea (90 mM urea and 55 mM TMAO) at days 0, 14, or 28. Further details regarding methodology are provided in Example 1.

Provided herein are tissue culture media supplements to promote development of tissue properties of engineered tissue in culture.

The present disclosure is based at least in part on the observation that immature bovine chondrocytes cultured in the presence of trimethylamine N-oxide (TMAO) or TMAO and urea yield cultured cartilage tissue that is significantly stiffer tissue (e.g., nearly two-fold higher Young's modulus) than the control group (see e.g., Example 1, Example 2).

As shown herein, TMAO can be included in a cell culture medium, such as a chondrogenic cell culture medium. Also, TMAO and urea can be included in a cell culture medium, such as a chondrogenic cell culture medium. Further, mature tissue constructs can be digested with chondroitinase to increase collagen content or improve mechanical properties. A cell culture medium including TMAO can be used to produce cartilage tissue with enhanced physical characteristics. Cells can be cultured in a TMAO-containing medium in or on a matrix or scaffold. The cells cultured in a TMAO-containing medium, matrix or scaffold containing such, can be used in vitro or in vivo methods for regenerating connective tissue, such as cartilage. For example, the cells cultured in a TMAO-containing medium, a matrix or scaffold containing such, or connective tissue produced from such, can be grafted or implanted into a subject. These and other features are described in more detail below.

Tissue Culture

One aspect provides a tissue culture medium containing TMAO.

Tissue culture is generally understood as the growth of eukaryotic cells in vitro. Tissue culture media and processes are well known (see e.g., Helgason and Miller 2004 Basic Cell Culture Protocols, 3d Ed., Humana Press, ISBN-10 1588292843; Vunjak-Nokakovic and Freshney, ed. 2006 Culture of Cells for Tissue Engineering, Wiley-Liss, ISBN-10 0471629359; Freshney 2005 Culture of Animal Cells, 5$^{th}$ ed., Wiley-Liss, ISBN-10 0471453293. Except as otherwise noted herein, therefore, the media and processes of the present invention can be according to any tissue culture media and processes known in the art.

A tissue culture medium can include various hormones or growth factors. The medium can be a chondrogenic tissue culture medium.

TMAO can be included in a tissue culture medium at a concentration of about 1 mM to about 1,000 mM. For example, TMAO can be included in a tissue culture medium at a concentration of about 5 mM, about 10 mM, about 20 mM, about 30 mM, about 40 mM, about 50 mM, about 60 mM, about 70 mM, about 80 mM, about 90 mM, about 100 mM, about 110 mM, about 120 mM, about 130 mM, about 140 mM, about 150 mM, about 160 mM, about 170 mM, about 180 mM, about 190 mM, about 200 mM, about 250 mM, about 300 mM, about 400 mM, about 450 mM, about 500 mM, about 550 mM, about 600 mM, about 650 mM, about 700 mM, about 750 mM, about 800 mM, about 850 mM, about 900 mM, about 950 mM, or about 1,000 mM. As another example, TMAO can be included in a tissue culture medium at a concentration of at least about 5 mM up to about 100 mM.

Urea can be included in a tissue culture medium at a concentration of about 1 mM to about 1,000 mM. For example, urea can be included in a tissue culture medium at a concentration of about 10 mM, about 20 mM, about 30 mM, about 40 mM, about 50 mM, about 60 mM, about 70 mM, about 80 mM, about 90 mM, about 100 mM, about 110 mM, about 120 mM, about 130 mM, about 140 mM, about 150 mM, about 160 mM, about 170 mM, about 180 mM, about 190 mM, about 200 mM, about 250 mM, about 300 mM, about 400 mM, about 450 mM, about 500 mM, about 550 mM, about 600 mM, about 650 mM, about 700 mM, about 750 mM, about 800 mM, about 850 mM, about 900 mM, about 950 mM, or about 1,000 mM.

Urea can be included in a tissue culture medium at a ratio (TMAO:urea) of about 100:1 to about 1:100. For example, urea can be included in a tissue culture medium at a ratio (TMAO:urea) of about 100:1, about 90:1, about :1, about 80:1, about 70:1, about 60:1, about 50:1, about 40:1, about 30:1, about 20:1, about 10:1, about 9:1, about 8:1, about 7:1, about 6:1, about 5:1, about 4:1, about 3:1, about 2:1, about 1:1, about 1:2, about 1:3, about 1:4, about 1:5, about 1:6, about 1:7, about 1:8, about 1:9, about 1:10, about 1:20, about 1:30, about 1:40, about 1:50, about 1:60, about 1:70, about 1:80, about 1:90, or about 1:100.

The tissue culture media can include chondroitinase (cABC). Digestion of mature tissue engineered constructs with chondroitinase (cABC) temporarily suppresses the glycosaminoglycan (GAG) content, increases the collagen content and improves the mechanical properties (see Bian 2009 Tissue Eng Tissue Eng Part A 15(8), 2065-2072). As shown herein, TMAO in combination with controlled cABC enzymatic treatment can provide increased collagen content in engineered cartilage (see e.g., Example 2). The cABC can be added to existing tissue culture media or added with fresh tissue culture media. Controlled digestion with cABC in the culture media can occur when tissue engineered constructs are nearly mature, substantially mature, or mature. cABC can be present in the tissue culture media at a concentration of at least about 0.01 U/mL. For example, cABC can be present in the tissue culture media at a concentration of at least about 0.01 U/mL, at least about 0.02 U/mL, at least about 0.03 U/mL, at least about 0.04 U/mL, at least about 0.05 U/mL, at least about 0.06 U/mL, at least about 0.07 U/mL, at least about 0.08 U/mL, at least about 0.09/mL, at least about 0.10 U/mL, at least about 0.11 U/mL, at least about 0.12/mL, at least about 0.13 U/mL, at least about 0.14 U/mL, at least about 0.15 U/mL, at least about 0.16 U/mL, at least about 0.17 U/mL, at least about 0.18 U/mL, at least about 0.19 U/mL, at least about 0.20 U/mL, at least about 0.25 U/mL, at least about 0.30 U/mL, at least about 0.40 U/mL, at least about 0.50 U/mL, at least about 0.60 U/mL, at least about 0.70 U/mL, at least about 0.80 U/mL, at least about 0.90 U/mL, at least about 1.0 U/mL, at least about 1.1 U/mL, at least about 1.2 U/mL, at least about 1.3 U/mL, at least about 1.4 U/mL, at least about 1.5 U/mL, or more.

Cells and Tissue

Described herein are methods for culturing cells to produce tissue with enhanced GAG production or collagen production. Methods described herein include culturing cells to produce connective tissue with enhanced mechanical properties.

The connective tissue can be any tissue including cells, fibers, and extracellular matrix. Some connective tissue may not include fibers (e.g., adipose tissue and blood). The connective tissue can The connective tissue can include collagen. The connective tissue can include collagenous fibers, elastic fibers, or reticular fibers. The connective tissue can be tissue that occurs in tendons, blood, cartilage, bone, adipose tissue, or lymphatic tissue. The connective tissue can be embryonic connective tissue, proper connective tissue (e.g., dense regular connective tissue, dense irregular connective tissue, or loose connective tissue), or special connective tissue (e.g., cartilage, bone, adipose tissue, blood, hematopoietic tissue or lymphatic tissue. The connective tissue can be, for example, cartilage.

The tissue (e.g., connective tissue) formed according to compositions and methods described herein can have enhanced mechanical properties as compared to tissue not so cultured. The cultured tissue can be nucleus pulposus (spine tissue). The cultured connective tissue can be cartilage tissue. The cultured cartilage tissue can have increased collagen content. The enhanced mechanical properties can include increased stiffness. Stiffness can be measured according to methods know in the art. For example, stiffness can be according to Young's modulus, also known as the tensile modulus, which is a measure of the stiffness of an isotropic elastic material. Tensile modulus is generally understood as the ratio of the uniaxial stress over the uniaxial strain in the range of stress in which Hooke's Law holds.

The cultured cells can be progenitor cells. The progenitor cell is generally of a type that can give rise to the target tissue(s) of interest. For example, the cultured progenitor cell can be a cell that can differentiate into connective tissue cells. Progenitor cells can be isolated, purified, and/or cultured by a variety of means known to the art. Methods for the isolation and culture of progenitor cells are discussed in, for example, Vunjak-Novakovic and Freshney (2006) Culture of Cells for Tissue Engineering, Wiley-Liss, ISBN 0471629359. In some embodiments, progenitors cells can be from the same subject into which cultured tissue is to be grafted or implanted. In other embodiments, progenitor cells can be derived from the same or different species as an intended transplant subject. For example, progenitor cells can be derived from an animal, including, but not limited to, a vertebrate such as a mammal, a reptile, or an avian. In some configurations, a mammal or avian is preferably a horse, a cow, a dog, a cat, a sheep, a pig, or a chicken, and most preferably a human.

Tissue progenitor cells of the present teachings include cells capable of differentiating into a target tissue, and/or undergoing morphogenesis to form the target tissue. Non-limiting examples of tissue progenitor cells include mesenchymal stem cells (MSCs), cells differentiated from MSCs, osteoblasts, chondrocytes, and fibroblastic cells such as interstitial fibroblasts, tendon fibroblasts, dermal fibroblasts, ligament fibroblasts, periodontal fibroblasts such as gingival fibroblasts, and craniofacial fibroblasts. Exemplary progenitor cells that can form cartilage tissue include, but are not limited to, a colony-forming unit-fibroblast (CFU-F), mesenchymal stem cell (MSC), an osteochondrogenic MSC, a chondrogenic MSC, a chondrocyte, or a hypertrophic chondrocyte. As another example, the progenitor cell can be a cell that undergoes endochondral ossification.

Tissue progenitor cells can be progenitor cells that can give rise to cartilage tissue such as MSCs or MSC chondrocytes. It is understood that MSC chondrocytes are chondrocytes differentiated from MSCs. In various configurations, the cartilage progenitor cells can form hyaline cartilage, elastic cartilage, or fibrocartilage so as to approximate the structure and function of the target tissue being modeled.

Cells cultured in the presence of TMAO can form connective tissue having increased stiffness. The connective tissue can include cartilage. The cultured cartilage tissue can have increased collagen content. Cartilage is generally understood as a stiff and inflexible connective tissue, which is not as hard or rigid as bone but is stiffer and less flexible than muscle. The cartilage tissue formed according to methods described herein can comprise chondrocytes. The chondrocytes of the cartilage can produce an extracellular matrix composed of Type II collagen fibers or Type I collagen fibers (e.g., fibrocartilage), proteoglycans, and elastin fibers. The cartilage tissue formed according to methods described herein can be elastic cartilage, hyaline cartilage or fibrocartilage, or a combination thereof. As understood in the art, elastic cartilage, hyaline cartilage and fibrocartilage differ according to types and proportion of collagen fibers, proteoglycans, and elastin fibers.

The cells cultured under conditions described herein can undergo chondrification (i.e., chondrogenesis). Chondrification can include condensed mesenchyme tissue differentiating into chondrocytes. Chondrification can include chondrocyte secretion of an extracellular matrix.

In some embodiments, the progenitor cells can comprise a heterologous nucleic acid so as to express a bioactive molecule such as heterologous protein, or to overexpress an endogenous protein. In non-limiting example, progenitor cells can express a fluorescent protein marker, such as GFP, EGFP, BFP, CFP, YFP, or RFP. In another example, progenitor cells can express a growth factor, such as activin A, adrenomedullin, aFGF, ALK1, ALK5, ANF, angiogenin, angiopoietin-1, angiopoietin-2, angiopoietin-3, angiopoietin-4, angiostatin, angiotropin, angiotensin-2, AtT20-ECGF, betacellulin, bFGF, B61, bFGF inducing activity, cadherins, CAM-RF, cGMP analogs, ChDI, CLAF, claudins, collagen, collagen receptors $\alpha_1\beta_1$ and $\alpha_2\beta_1$, connexins, Cox-2, ECDGF (endothelial cell-derived growth factor), ECG, ECI, EDM, EGF, EMAP, endoglin, endothelins, endostatin, endothelial cell growth inhibitor, endothelial cell-viability maintaining factor, endothelial differentiation sphingolipid G-protein coupled receptor-1 (EDG1), ephrins, Epo, HGF, TNF-alpha, TGF-beta, PD-ECGF, PDGF, IGF, IL8, growth hormone, fibrin fragment E, FGF-5, fibronectin and fibronectin receptor $\alpha_5\beta_1$, Factor X, HB-EGF, HBNF, HGF, HUAF, heart derived inhibitor of vascular cell proliferation, IFN-gamma, IL1, IGF-2 IFN-gamma, integrin receptors (e.g., various combinations of α subunits (e.g., $\alpha_1, \alpha_2, \alpha_3, \alpha_4, \alpha_5, \alpha_6, \alpha_7, \alpha_8, \alpha_9, \alpha_E, \alpha_V, \alpha_{IIb}, \alpha_L, \alpha_M, \alpha_X$), K-FGF, LIF, leiomyoma-derived growth factor, MCP-1, macrophage-derived growth factor, monocyte-derived growth factor, MD-ECI, MECIF, MMP 2, MMP3, MMP9, urokinase plasminogen activator, neuropilin (NRP1, NRP2), neurothelin, nitric oxide donors, nitric oxide synthases (NOSs), notch, occludins, zona occludins, oncostatin M, PDGF, PDGF-B, PDGF receptors, PDGFR-β, PD-ECGF, PAI-2, PD-ECGF, PF4, P1GF, PKR1, PKR2, PPAR-gamma, PPAR-gamma ligands, phosphodiesterase, prolactin, prostacyclin, protein S, smooth muscle cell-derived growth factor, smooth muscle cell-derived migration factor, sphingosine-1-phosphate-1 (S1P1), Syk, SLP76, tachykinins, TGF-beta, Tie 1, Tie2, TGF-β, and TGF-β receptors, TIMPs, TNF-alpha, TNF-beta, transferrin, thrombospondin, urokinase, VEGF-A, VEGF-B, VEGF-C, VEGF-D, VEGF-E, VEGF, VEGF.sub.164, VEGI, EG-VEGF, VEGF receptors, PF4, 16 kDa fragment of prolactin, prostaglandins E1 and E2, steroids, heparin, 1-butyryl glycerol (monobutyrin), or nicotinic amide. As another example, progenitor cells introduced to a matrix can comprise genetic sequences that reduce or eliminate an immune response in the host (e.g., by suppressing expression of cell surface antigens such as class I and class II histocompatibility antigen).

Matrix

Various compositions and methods described herein employ a matrix. In some embodiments, progenitor cells are introduced into or onto the matrix so as to form a tissue module. In various embodiments, the matrix materials are formed into a 3-dimensional scaffold. The scaffold can contain one or more matrix layers.

The matrix or scaffold can: provide structural or functional features of the target connective tissue (e.g., cartilage); allow cell attachment and migration; deliver and retain cells and biochemical factors; enable diffusion of cell nutrients and expressed products; or exert certain mechanical and biological influences to modify the behavior of the cell phase. The matrix materials of various embodiments are biocompatible materials that generally form a porous, microcellular scaffold, which provides a physical support and an adhesive substrate for introducing progenitor cells during in vitro fabrication or culturing and subsequent in vivo implantation.

A matrix with a high porosity and an adequate pore size is preferred so as to facilitate cell introduction and diffusion throughout the whole structure of both cells and nutrients. Matrix biodegradability is also preferred since absorption of the matrix by the surrounding tissues (e.g., after differentiation and growth of cartilage tissues from progenitor cells) can eliminate the necessity of a surgical removal. The rate at which degradation occurs should coincide as much as possible with the rate of tissue formation. Thus, while cells are fabricating their own natural structure around themselves, the matrix can provide structural integrity and eventually break down leaving the neotissue, newly formed tissue which can assume the mechanical load. Injectability is also preferred in some clinical applications. Suitable matrix materials are discussed in, for example, Ma and Elisseeff, ed. (2005) Scaffolding in Tissue Engineering, CRC, ISBN 1574445219; Saltzman (2004) Tissue Engineering: Engineering Principles for the Design of Replacement Organs and Tissues, Oxford ISBN 019514130X.

The matrix configuration can be dependent on the connective tissue that is to be produced. Preferably the matrix is a pliable, biocompatible, porous template that allows for target tissue growth. The matrix can be fabricated into structural supports, where the geometry of the structure is tailored to the application. The porosity of the matrix is a design parameter that influences cell introduction or cell infiltration. The matrix can be designed to incorporate extracellular matrix proteins that influence cell adhesion and migration in the matrix.

Matrices can be produced from proteins (e.g. extracellular matrix proteins such as fibrin, collagen, and fibronectin), polymers (e.g., polyvinylpyrrolidone), polysaccharides (e.g. alginate), hyaluronic acid, or analogs, mixtures, combinations, and derivatives of the above.

The matrix can be formed of synthetic polymers. Such synthetic polymers include, but are not limited to, poly(ethylene)glycol, bioerodible polymers (e.g., poly(lactide), poly(glycolic acid), poly(lactide-co-glycolide), poly(caprolactone), polyester (e.g., poly-(L-lactic acid), polyanhydride, polyglactin, polyglycolic acid), polycarbonates, polyamides, polyanhydrides, polyamino acids, polyortho esters, polyacetals, polycyanoacrylates), polyphosphazene, degradable polyurethanes, non-erodible polymers (e.g., polyacrylates, ethylene-vinyl acetate polymers and other acyl substituted cellulose acetates and derivatives thereof), non-erodible polyurethanes, polystyrenes, polyvinyl chloride, polyvinyl fluoride, polyvinyl pyrrolidone, poly(vinylimidazole), chlorosulphonated polyolefins, polyethylene oxide, polyvinyl alcohol (e.g., polyvinyl alcohol sponge), synthetic marine adhesive proteins, Teflon®, nylon, or analogs, mixtures, combinations (e.g., polyethylene oxide-polypropylene glycol block copolymer; poly(D,L-lactide-co-glycolide) fiber matrix), and derivatives of the above.

The matrix can be formed of naturally occurring polymers or natively derived polymers. Such polymers include, but are not limited to, agarose, alginate (e.g., calcium alginate gel), fibrin, fibrinogen, fibronectin, collagen (e.g., a collagen gel), gelatin, hyaluronic acid, chitin, and other suitable polymers and biopolymers, or analogs, mixtures, combinations, and derivatives of the above. Also, the matrix can be formed from a mixture of naturally occurring biopolymers and synthetic polymers.

In some embodiments, one or more matrix materials are modified so as to increase biodegradability. For example, PCL is a biodegradable polyester by hydrolysis of its ester linkages in physiological conditions, and can be further modified with ring opening polymerization to increase its biodegradability.

Introduction of Cells to Matrix

Progenitor cells can be introduced into the matrix material by a variety of means known to the art. Methods for the introduction (e.g., infusion, seeding, injection, etc.) of progenitor cells into or into the matrix material are discussed in, for example, Ma and Elisseeff, ed. (2005) Scaffolding In Tissue Engineering, CRC, ISBN 1574445219; Saltzman (2004) Tissue Engineering: Engineering Principles for the Design of Replacement Organs and Tissues, Oxford ISBN 019514130X; Minuth et al. (2005) Tissue Engineering: From Cell Biology to Artificial Organs, John Wiley & Sons, ISBN 3527311866. For example, progenitor cells can be introduced into or onto the matrix by methods including hydrating freeze-dried scaffolds with a cell suspension. Methods of addition of additional agents can vary, as will be understood in the art.

Methods of culturing and differentiating progenitor cells in or on scaffolds are generally known in the art (see e.g., Saltzman (2004) Tissue Engineering: Engineering Principles for the Design of Replacement Organs and Tissues, Oxford ISBN 019514130X; Vunjak-Novakovic and Freshney, eds. (2006) Culture of Cells for Tissue Engineering, Wiley-Liss, ISBN 0471629359; Minuth et al. (2005) Tissue Engineering: From Cell Biology to Artificial Organs, John Wiley & Sons, ISBN 3527311866). As will be appreciated by one skilled in the art, the time between progenitor cell introduction into or onto the matrix and engrafting the resulting matrix can vary according to particular application. Incubation (and subsequent replication and/or differentiation) of the engineered composition containing cartilage progenitor cells in or on the matrix material can be, for example, at least in part in vitro, substantially in vitro, at least in part in vivo, or substantially in vivo. Determination of optimal culture time is within the skill of the art. A suitable medium can be used for in vitro progenitor cell infusion, differentiation, or cell transdifferentiation (see e.g., Vunjak-Novakovic and Freshney, eds. (2006) Culture of Cells for Tissue Engineering, Wiley-Liss, ISBN 0471629359; Minuth et al. (2005) Tissue Engineering: From Cell Biology to Artificial Organs, John Wiley & Sons, ISBN 3527311866). The culture time can vary from about an hour, several hours, a day, several days, a week, or several weeks. The quantity and type of cells present in the matrix can be characterized by, for example, morphology by ELISA, by protein assays, by genetic assays, by mechanical analysis, by RT-PCR, and/or by immunostaining to screen for cell-type-specific markers (see e.g., Minuth et al. (2005) Tissue Engineering: From Cell Biology to Artificial Organs, John Wiley & Sons, ISBN 3527311866).

For tissue modules using small scaffolds (<100 cubic millimeters in size), in vitro medium can be changed manually, and additional agents added periodically (e.g., every 3-4 days). For larger scaffolds, the culture can be maintained, for example, in a bioreactor system, which may use a minipump for medium change. The minipump can be housed in an incubator, with fresh medium pumped to the matrix material of the scaffold. The medium circulated back to, and through, the matrix can have about 1% to about 100% fresh medium. The pump rate can be adjusted for optimal distribution of medium and/or additional agents included in the medium. The medium delivery system can be tailored to the type of tissue or organ being manufactured. All culturing can be performed under sterile conditions.

Density of progenitor cells (e.g., cartilage progenitor cells) (and their lineage derivatives) can be optimized so as to maximize the regenerative outcome of a connective tissue module. Cell densities in a matrix can be monitored over time and at end-points. Tissue properties can be determined, for example, using standard techniques known to skilled artisans, such as histology, structural analysis, immunohistochemistry, biochemical analysis, and mechanical properties. As will be recognized by one skilled in the art, the cell densities of progenitor cells can vary according to, for example, progenitor type, tissue or organ type, matrix material, matrix volume, infusion method, seeding pattern, culture medium, growth factors, incubation time, incubation conditions, and the like. Generally, for cartilage progenitor cells, the cell density in a matrix can be, independently, from 0.0001 million cells (M) $ml^{-1}$ to about 1000 M $ml^{-1}$. For example, the tissue progenitor cells can each present in the matrix at a density of about 0.001 M $ml^{-1}$, 0.01 M $ml^{-1}$, 0.1 M $ml^{-1}$, 1 M $ml^{-1}$, 5 M $ml^{-1}$, 10 M $ml^{-1}$, 15 M $ml^{-1}$, 20 M $ml^{-1}$, 25 M $ml^{-1}$, 30 M $ml^{-1}$, 35 M $ml^{-1}$, 40 M $ml^{-1}$, 45 M $ml^{-1}$, 50 M $ml^{-1}$, 55 M $ml^{-1}$, 60 M $ml^{-1}$, 65 M $ml^{-1}$, 70 M $ml^{-1}$, 75 M $ml^{-1}$, 80 M $ml^{-1}$, 85 M $ml^{-1}$, 90 M $ml^{-1}$, 95 M $ml^{-1}$, 100 M $ml^{-1}$, 200 M $ml^{-1}$, 300 M $ml^{-1}$, 400 M $ml^{-1}$, 500 M $ml^{-1}$, 600 M $ml^{-1}$, 700 M $ml^{-1}$, 800 M $ml^{-1}$, or 900 M $ml^{-1}$.

In some embodiments, a tissue module can comprise progenitor cells at a density of about 0.0001 million cells (M) $ml^{-1}$ to about 1000 M $ml^{-1}$. In some configurations, a tissue module can comprise progenitor cells at a density of at least about 1 M $ml^{-1}$ up to about 100 M $ml^{-1}$. In some configurations, a tissue module can comprise progenitor cells at a density of at least about 5 M $ml^{-1}$ up to about 95 M $ml^{-1}$. In some configurations, a tissue module can comprise progenitor cells at a density of at least about 10 M $ml^{-1}$ up to about 90 M $ml^{-1}$. In some configurations, a tissue module can comprise progenitor cells at a density of at least about 15 M $ml^{-1}$ up to about 85 M $ml^{-1}$. In some configurations, a tissue module can comprise progenitor cells at a density of at least about 20 M $ml^{-1}$ up to about 80 M $ml^{-1}$. In some configurations, a tissue module can comprise progenitor cells at a density of at least about 25 M $ml^{-1}$ up to about 75 M $ml^{-1}$. In some configurations, a tissue module can comprise progenitor cells at a density of at least about 30 M $ml^{-1}$ up to about 70 M $ml^{-1}$. In some configurations, a tissue module can comprise progenitor cells at a density of at least about 35 M $ml^{-1}$ up to about 65 M $ml^{-1}$. In some configurations, a tissue module can comprise progenitor cells at a density of at least about 40 M ml$^{-1}$ up to about 60 M ml$^{-1}$. In some configurations, a tissue module can comprise progenitor cells at a density of at least about 45 M ml$^{-1}$ up to about 55 M ml$^{-1}$. In some configurations, a tissue module can comprise progenitor cells at a density of at least about 45 M ml$^{-1}$ up to about 50 M ml$^{-1}$. In some configurations, a tissue module can comprise progenitor cells at a density of at least about 50 M ml$^{-1}$ up to about 55 M ml$^{-1}$.

In some embodiments, one or more cell types in addition to a first type of cartilage progenitor cells can be introduced into or onto the matrix material. Such additional cell type can be selected from those discussed above, and/or can include (but not limited to) skin cells, liver cells, heart cells, kidney cells, pancreatic cells, lung cells, bladder cells, stomach cells, intestinal cells, cells of the urogenital tract, breast cells, skeletal muscle cells, skin cells, bone cells, cartilage cells, keratinocytes, hepatocytes, gastro-intestinal cells, epithelial cells, endothelial cells, mammary cells, skeletal muscle cells, smooth muscle cells, parenchymal cells, osteoclasts, or chondrocytes. These cell-types can be introduced prior to, during, or after introduction of the first type of cartilage progenitor cells. Such introduction may take place in vitro or in vivo. When the cells are introduced in vivo, the introduction may be at the site of the tissue module or at a site removed therefrom. Exemplary routes of administration of the cells include injection and surgical implantation.

Formulation

The agents and compositions described herein can be formulated by any conventional manner using one or more pharmaceutically acceptable carriers or excipients as described in, for example, Remington's Pharmaceutical Sciences (A. R. Gennaro, Ed.), 21st edition, ISBN: 0781746736 (2005), incorporated herein by reference in its entirety. Such formulations will contain a therapeutically effective amount of a biologically active agent described herein, preferably in purified form, together with a suitable amount of carrier so as to provide the form for proper administration to the subject.

The formulation should suit the mode of administration. The agents of use with the current invention can be formulated by known methods for administration to a subject using several routes which include, but are not limited to, parenteral, pulmonary, oral, topical, intradermal, intramuscular, intraperitoneal, intravenous, subcutaneous, intranasal, epidural, ophthalmic, buccal, and rectal. The individual agents may also be administered in combination with one or more additional agents or together with other biologically active or biologically inert agents. Such biologically active or inert agents may be in fluid or mechanical communication with the agent(s) or attached to the agent(s) by ionic, covalent, Van der Waals, hydrophobic, hydrophilic or other physical forces.

Controlled-release (or sustained-release) preparations may be formulated to extend the activity of the agent(s) and reduce dosage frequency. Controlled-release preparations can also be used to effect the time of onset of action or other characteristics, such as blood levels of the agent, and consequently affect the occurrence of side effects. Controlled-release preparations may be designed to initially release an amount of an agent(s) that produces the desired therapeutic effect, and gradually and continually release other amounts of the agent to maintain the level of therapeutic effect over an extended period of time. In order to maintain a near-constant level of an agent in the body, the agent can be released from the dosage form at a rate that will replace the amount of agent being metabolized or excreted from the body. The controlled-release of an agent may be stimulated by various inducers, e.g., change in pH, change in temperature, enzymes, water, or other physiological conditions or molecules.

Agents or compositions described herein can also be used in combination with other therapeutic modalities, as described further below. Thus, in addition to the therapies described herein, one may also provide to the subject other therapies known to be efficacious for treatment of the disease, disorder, or condition.

Molecular Engineering

Host cells can be transformed using a variety of standard techniques known to the art (see, e.g., Sambrook and Russel (2006) Condensed Protocols from Molecular Cloning: A Laboratory Manual, Cold Spring Harbor Laboratory Press, ISBN-10: 0879697717; Ausubel et al. (2002) Short Protocols in Molecular Biology, 5th ed., Current Protocols, ISBN-10: 0471250929; Sambrook and Russel (2001) Molecular Cloning: A Laboratory Manual, 3d ed., Cold Spring Harbor Laboratory Press, ISBN-10: 0879695773; Elhai, J. and Wolk, C. P. 1988. Methods in Enzymology 167, 747-754). Such techniques include, but are not limited to, viral infection, calcium phosphate transfection, liposome-mediated transfection, microprojectile-mediated delivery, receptor-mediated uptake, cell fusion, electroporation, and the like. The transfected cells can be selected and propagated to provide recombinant host cells that comprise the expression vector stably integrated in the host cell genome.

Methods of down-regulation or silencing genes are known in the art. For example, expressed protein activity can be down-regulated or eliminated using antisense oligonucleotides, protein aptamers, nucleotide aptamers, and RNA interference (RNAi) (e.g., small interfering RNAs (sRNA), short hairpin RNA (shRNA), and micro RNAs (miRNA) (see e.g., Fanning and Symonds (2006) Handb Exp Pharmacol. 173, 289-303G, describing hammerhead ribozymes and small hairpin RNA; Helene, C., et al. (1992) Ann. N.Y. Acad. Sci. 660, 27-36; Maher (1992) Bioassays 14(12): 807-15, describing targeting deoxyribonucleotide sequences; Lee et al. (2006) Curr Opin Chem Biol. 10, 1-8, describing aptamers; Reynolds et al. (2004) Nature Biotechnology 22(3), 326-330, describing RNAi; Pushparaj and Melendez (2006) Clinical and Experimental Pharmacology and Physiology 33(5-6), 504-510, describing RNAi; Dillon et al. (2005) Annual Review of Physiology 67, 147-173, describing RNAi; Dykxhoorn and Lieberman (2005) Annual Review of Medicine 56, 401-423, describing RNAi). RNAi molecules are commercially available from a variety of sources (e.g., Ambion, TX; Sigma Aldrich, MO; Invitrogen). Several sRNA molecule design programs using a variety of algorithms are known to the art (see e.g., Cenix algorithm, Ambion; BLOCK-iT™ RNAi Designer, Invitrogen; sRNA Whitehead Institute Design Tools, Bioinformatics & Research Computing). Traits influential in defining optimal sRNA sequences include G/C content at the termini of the siRNAs, Tm of specific internal domains of the siRNA, siRNA length, position of the target sequence within the CDS (coding region), and nucleotide content of the 3' overhangs.

Therapeutic Methods

Also provided is a process of treating a tissue defect, such as a connective tissue defect, in a subject in need administration of a therapeutically effective amount of progenitor cells cultured in a TMAO-containing medium described herein or connective tissue produced therefrom.

Various embodiments provide a method of treating a tissue defect in a subject by implanting a tissue module described herein into a subject in need thereof. A determination of the need for treatment will typically be assessed by a history and physical exam consistent with the tissue defect at issue. A subject in need of the therapeutic methods described herein can be a subject having, diagnosed with, suspected of having, or at risk for developing a tissue defect. Subjects with an identified need of therapy include those with a diagnosed tissue defect. A determination of the need for treatment will typically be assessed by a history and physical exam consistent with the disease or condition at issue. Diagnosis of the various conditions treatable by the methods described herein is within the skill of the art. The subject is preferably an animal, including, but not limited to, mammals, reptiles, and avians, more preferably horses, cows, dogs, cats, sheep, pigs, and chickens, and most preferably human.

As an example, a subject in need may have damage to a tissue, and the method provides an increase in biological function of the tissue by at least 5%, 10%, 25%, 50%, 75%, 90%, 100%, or 200%, or even by as much as 300%, 400%, or 500%. As yet another example, the subject in need may have a disease, disorder, or condition, and the method provides an engineered tissue module sufficient to ameliorate or stabilize the disease, disorder, or condition. For example, the subject may have a disease, disorder, or condition that results in the loss, atrophy, dysfunction, or death of connective tissue cells. Exemplary treated conditions include arthritis; osteoarthritis; osteoporosis; osteochondrosis; osteochondritis; osteogenesis imperfecta; osteomyelitis; osteophytes (i.e., bone spurs); achondroplasia; costochondritis; chondroma; chondrosarcoma; herniated disk; Klippel-Feil syndrome; osteitis deformans; osteitis fibrosa cystica, a congenital defect that results in the absence of a tissue; accidental tissue defect or damage such as fracture, wound, or joint trauma; an autoimmune disorder; diabetes (e.g., Charcot foot); cancer; a disease, disorder, or condition that requires the removal of a tissue (e.g., tumor resection); Marfan syndrome; scurvy; Ehlers-Danlos syndrome; Loeys-Dietz syndrome; Pseudoxanthoma elasticum; systemic lupus erythematosus; osteogenesis imperfecta (brittle bone disease); fibrodysplasia ossificans progressiva; spontaneous pneumothorax; or sarcoma. In a further example, the subject in need may have an increased risk of developing a disease, disorder, or condition that is delayed or prevented by the method.

Implantation of a connective tissue module described herein is within the skill of the art. The matrix and/or cellular assembly can be either fully or partially implanted into a tissue or organ of the subject to become a functioning part thereof. In some embodiments, the implant initially attaches to and communicates with the host through a cellular monolayer. In some embodiments, over time, the introduced cells can expand and migrate out of the polymeric matrix to the surrounding tissue. After implantation, cells surrounding the tissue module can enter through cell migration. The cells surrounding the tissue module can be attracted by biologically active materials, including biological response modifiers, such as polysaccharides, proteins, peptides, genes, antigens, and antibodies which can be selectively incorporated into the matrix to provide the needed selectivity, for example, to tether the cell receptors to the matrix or stimulate cell migration into the matrix, or both. Generally, the matrix is porous, allowing for cell migration, augmented by both biological and physical-chemical gradients. For example, cells surrounding the implanted matrix can be attracted by biologically active materials including one ore more of VEGF, fibroblast growth factor, transforming growth factor-beta, endothelial cell growth factor, P-selectin, and intercellular adhesion molecule. One of skill in the art will recognize and know how to use other biologically active materials that are appropriate for attracting cells to the matrix.

The methods, compositions, and devices of the application can include concurrent or sequential treatment with one or more of enzymes, ions, growth factors, and biologic agents, such as thrombin and calcium, or combinations thereof. The methods, compositions, and devices of the application can include concurrent or sequential treatment with non-biologic and/or biologic drugs.

Administration

Agents and compositions described herein can be administered according to methods described herein in a variety of means known to the art. The agents and composition can be used therapeutically either as exogenous materials or as endogenous materials. Exogenous agents are those produced or manufactured outside of the body and administered to the body. Endogenous agents are those produced or manufactured inside the body by some type of device (biologic or other) for delivery within or to other organs in the body.

As discussed above, administration can be parenteral, pulmonary, oral, topical, intradermal, intramuscular, intraperitoneal, intravenous, subcutaneous, intranasal, epidural, ophthalmic, buccal, or rectal administration.

Agents and compositions described herein can be administered in a variety of methods well known in the arts. Administration can include, for example, methods involving oral ingestion, direct injection (e.g., systemic or stereotactic), implantation of cells engineered to secrete the factor of interest, drug-releasing biomaterials, polymer matrices, gels, permeable membranes, osmotic systems, multilayer coatings, microparticles, implantable matrix devices, mini-osmotic pumps, implantable pumps, injectable gels and hydrogels, liposomes, micelles (e.g., up to 30 µm), nanospheres (e.g., less than 1 µm), microspheres (e.g., 1-100 µm), reservoir devices, a combination of any of the above, or other suitable delivery vehicles to provide the desired release profile in varying proportions. Other methods of controlled-release delivery of agents or compositions will be known to the skilled artisan and are within the scope of the invention.

Delivery systems may include, for example, an infusion pump which may be used to administer the agent or composition in a manner similar to that used for delivering insulin or chemotherapy to specific organs or tumors. Typically, using such a system, an agent or composition is administered in combination with a biodegradable, biocompatible polymeric implant that releases the agent over a controlled period of time at a selected site. Examples of polymeric materials include polyanhydrides, polyorthoesters, polyglycolic acid, polylactic acid, polyethylene vinyl acetate, and copolymers and combinations thereof. In addition, a controlled release system can be placed in proximity of a therapeutic target, thus requiring only a fraction of a systemic dosage.

Agents can be encapsulated and administered in a variety of carrier delivery systems. Examples of carrier delivery systems include microspheres, hydrogels, polymeric implants, smart polymeric carriers, and liposomes (see generally, Uchegbu and Schatzlein, eds. (2006) Polymers in Drug Delivery, CRC, ISBN-10: 0849325331). Carrier-based systems for molecular or biomolecular agent delivery can: provide for intracellular delivery; tailor biomolecule/agent release rates; increase the proportion of biomolecule that reaches its site of action; improve the transport of the drug to its site of action; allow colocalized deposition with other agents or excipients; improve the stability of the agent in vivo; prolong the residence time of the agent at its site of action by reducing clearance; decrease the nonspecific delivery of the agent to nontarget tissues; decrease irritation caused by the agent; decrease toxicity due to high initial doses of the agent;

alter the immunogenicity of the agent; decrease dosage frequency, improve taste of the product; or improve shelf life of the product.

Kits

Also provided are kits. Such kits can include an agent or composition described herein and, in certain embodiments, instructions for administration. Such kits can facilitate performance of the methods described herein. When supplied as a kit, the different components of the composition can be packaged in separate containers and admixed immediately before use. Components include, but are not limited to a culture medium containing TMAO, as described herein. Such packaging of the components separately can, if desired, be presented in a pack or dispenser device which may contain one or more unit dosage forms containing the composition. The pack may, for example, comprise metal or plastic foil such as a blister pack. Such packaging of the components separately can also, in certain instances, permit long-term storage without losing activity of the components.

Kits may also include reagents in separate containers such as, for example, sterile water or saline to be added to a lyophilized active component packaged separately. For example, sealed glass ampules may contain a lyophilized component and in a separate ampule, sterile water, sterile saline or sterile each of which has been packaged under a neutral non-reacting gas, such as nitrogen. Ampules may consist of any suitable material, such as glass, organic polymers, such as polycarbonate, polystyrene, ceramic, metal or any other material typically employed to hold reagents. Other examples of suitable containers include bottles that may be fabricated from similar substances as ampules, and envelopes that may consist of foil-lined interiors, such as aluminum or an alloy. Other containers include test tubes, vials, flasks, bottles, syringes, and the like. Containers may have a sterile access port, such as a bottle having a stopper that can be pierced by a hypodermic injection needle. Other containers may have two compartments that are separated by a readily removable membrane that upon removal permits the components to mix. Removable membranes may be glass, plastic, rubber, and the like.

In certain embodiments, kits can be supplied with instructional materials. Instructions may be printed on paper or other substrate, and/or may be supplied as an electronic-readable medium, such as a floppy disc, mini-CD-ROM, CD-ROM, DVD-ROM, Zip disc, videotape, audio tape, and the like. Detailed instructions may not be physically associated with the kit; instead, a user may be directed to an Internet web site specified by the manufacturer or distributor of the kit.

Definitions and methods described herein are provided to better define the present invention and to guide those of ordinary skill in the art in the practice of the present invention. Unless otherwise noted, terms are to be understood according to conventional usage by those of ordinary skill in the relevant art.

In some embodiments, numbers expressing quantities of ingredients, properties such as molecular weight, reaction conditions, and so forth, used to describe and claim certain embodiments of the invention are to be understood as being modified in some instances by the term "about." In some embodiments, the term "about" is used to indicate that a value includes the standard deviation of the mean for the device or method being employed to determine the value. In some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements. The recitation of ranges of values herein is merely intended to serve as a shorthand method of referring individually to each separate value falling within the range. Unless otherwise indicated herein, each individual value is incorporated into the specification as if it were individually recited herein.

In some embodiments, the terms "a" and "an" and "the" and similar references used in the context of describing a particular embodiment (especially in the context of certain of the following claims) can be construed to cover both the singular and the plural, unless specifically noted otherwise. In some embodiments, the term "or" as used herein, including the claims, is used to mean "and/or" unless explicitly indicated to refer to alternatives only or the alternatives are mutually exclusive.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and can also cover other unlisted steps. Similarly, any composition or device that "comprises," "has" or "includes" one or more features is not limited to possessing only those one or more features and can cover other unlisted features.

All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience or patentability. When any such inclusion or deletion occurs, the specification is herein deemed to contain the group as modified thus fulfilling the written description of all Markush groups used in the appended claims.

All publications, patents, patent applications, and other references cited in this application are incorporated herein by reference in their entirety for all purposes to the same extent as if each individual publication, patent, patent application or other reference was specifically and individually indicated to be incorporated by reference in its entirety for all purposes. Citation of a reference herein shall not be construed as an admission that such is prior art to the present invention.

Having described the invention in detail, it will be apparent that modifications, variations, and equivalent embodiments are possible without departing the scope of the invention defined in the appended claims. Furthermore, it should be appreciated that all examples in the present disclosure are provided as non-limiting examples.

EXAMPLES

The following non-limiting examples are provided to further illustrate the present invention. It should be appreciated by those of skill in the art that the techniques disclosed in the examples that follow represent approaches the inventors have found function well in the practice of the invention, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the invention.

Example 1

This example demonstrates stiffening of cultured tissue with culture media containing Trimethylamine N-oxide (TMAO).

Immature bovine chondrocytes were enzymatically isolated and encapsulated in 2% w/v type VII agarose (Sigma). Engineered cylindrical constructs were cultured in serum-free chondrogenic media (ITS+, ascorbic acid, dexamethasone, pen/strep) and transforming growth factor beta-3 (TGFβ3) for the first 14 days.

The culture media of some constructs were supplemented from day 0 with TMAO (180 or 55 mM), urea (360 or 90 mM) or TMAO+urea (combo: 360 mM urea and 180 mM TMAO which is the physiological ratio found in shark tissue).

Results showed that the TMAO groups yield significantly stiffer tissue (e.g., nearly two-fold higher Young's modulus) than the control group by day 28 of culture (see e.g., FIG. 1).

Further preliminary results suggest that the combination of urea and TMAO at lower concentrations may also provide beneficial effects to tissue properties (data not shown).

Example 2

This example demonstrates stiffening of cultured tissue with culture media containing Trimethylamine N-oxide (TMAO).

Articular chondrocytes were harvested from juvenile bovine wrist joints (2-4 weeks old), and digested for 8 hrs at 37° C. with Collagenase V (Sigma) to isolate chondrocytes. The cells were expanded for one passage in DMEM media containing 10% FBS, 1% PSAM, 5 ng/ml bFGF, 10 ng/ml PDGF, and 1 ng/ml of TGF-b1 (plating density=180 cells/$cm^2$) (see Ng et al. 2010 Tissue Eng Part A 16(3), 1041-1051). The passaged cells were seeded in 2% w/v agarose hydrogel scaffold (Type VII, Sigma Inc.) at a concentration of 30M cells/ml. Samples were cored (diameter=4 mm, thickness=2.34 mm) and cultured in chondrogenically-defined media (CM: DMEM with 0.1 uM dexamethasone, 40 mg/mL L-proline, 50 mg/mL ascorbate 2-phosphate, 100 mg/mL sodium pyruvate, 1×ITS+premix, 100 U/ml penicillin, and 100 mg/ml streptomycin and amphotericin B) supplemented with TGF-$\beta_3$ for the first 14 days. Constructs grown without TMAO served as control.

Six culture medias were evaluated, with serum free media containing ascorbic acid and 10 ng/ml of TGF-b3 for the first 14 days used as the control (see Lima et al. 2007 Osteoarthritis Cartilage 15(9), 1025-1033). TMAO was added to the media at concentrations of 55 mM and 180 mM, and urea was added to the media at concentrations of 90 mM and 360 mM. The final group included a combination (combo) of TMAO (180 mM) and urea (360 mM).

The equilibrium Young's ($E_\gamma$) and dynamic modulus was determined under 10% unconfined compression. Biochemical analysis was performed to determine the GAG, hydroxyproline (OHP) and DNA content. GAG and OHP values were normalized to the DNA content and wet weight. Tested samples were fixed for histology and stained with Picosirius Red and Safranin-O to determine the distribution of collagen and GAG, respectively. Mechanical, biochemical and histological analysis was performed every two weeks (n=4/5). A two-way ANOVA (factors: culture day and treatment) was performed to evaluate the treatment for mechanical and biochemical analysis with a Bonferroni post hoc analysis.

Figure 2:
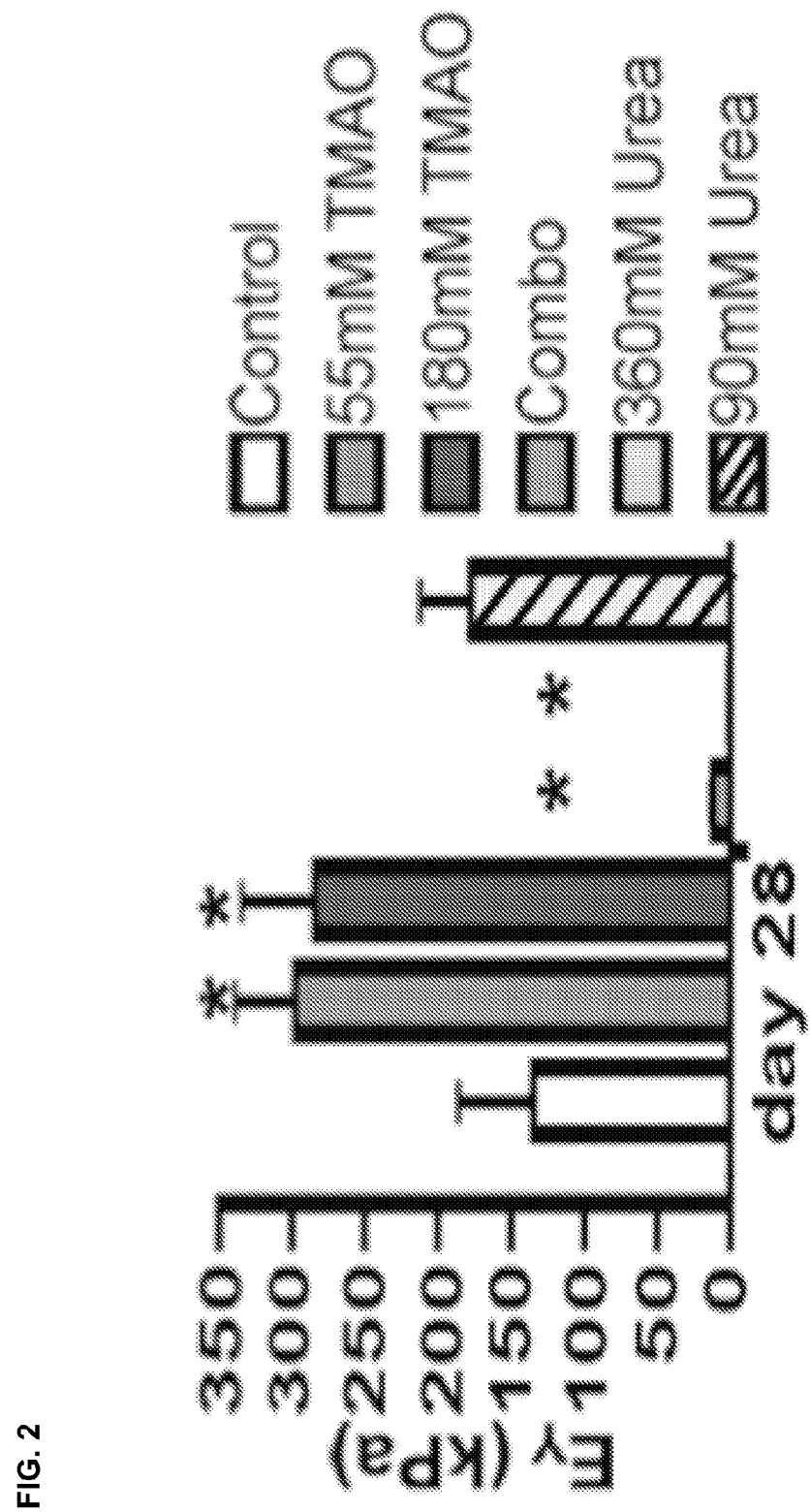
FIG. 2 is a bar graph of the mechanical properties (Young's modulus, $E\gamma$, kPa) of articular chondrocytes cultured with TMAO (180 or 55 mM), urea (360 or 90 mM), or a combination of TMAO and urea (360 mM urea and 180 mM TMAO). *$p \leq 0.05$ vs. control, one-way ANOVA with a Bonferroni post hoc test. Further details regarding methodology are provided in Example 2.

Results showed that by day 28, the mechanical properties of the 55 mM and 180 mM TMAO groups were 2× greater than the control group (see e.g., FIG. 2). The dynamic modulus followed a similar trend across groups (data not shown).

Figure 3:
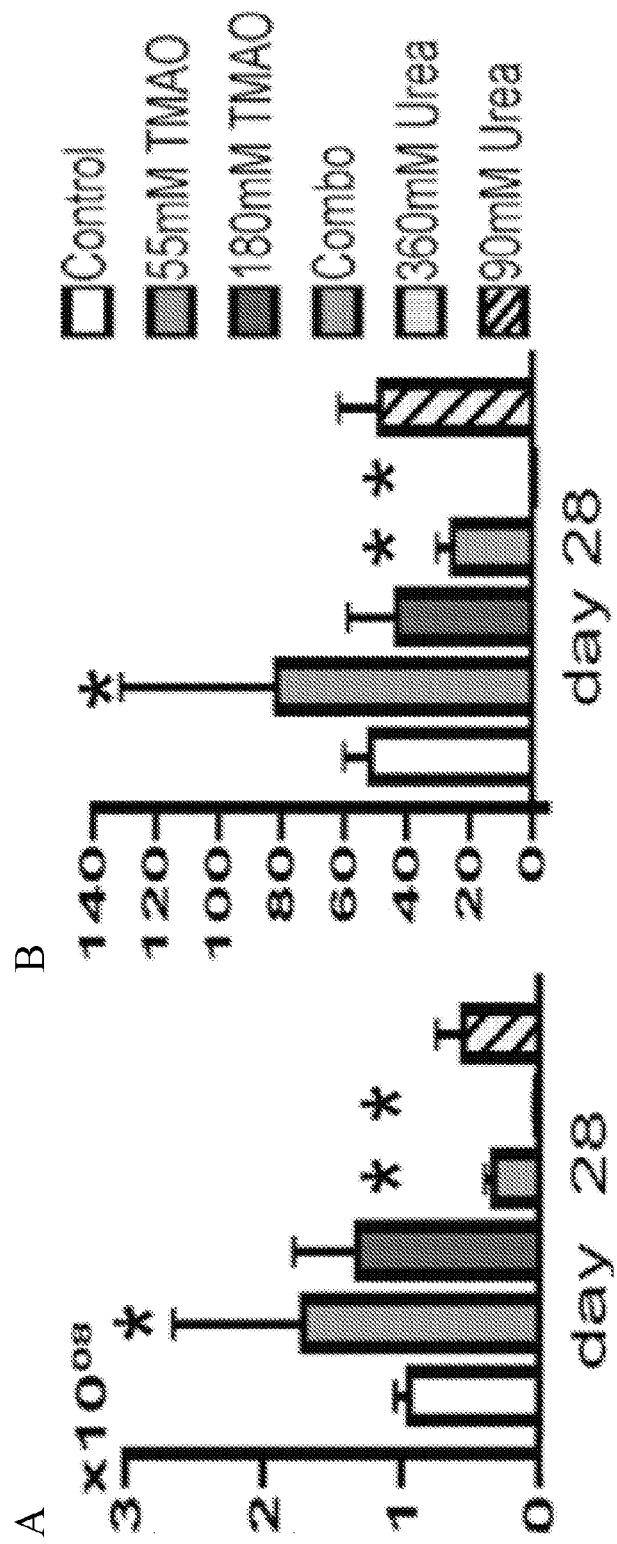
FIG. 3 is a series of bar graphs showing normalized GAG content (FIG. 3A) and normalized OHP content (FIG. 3B) for articular chondrocytes cultured with TMAO (180 or 55 mM), urea (360 or 90 mM), or a combination of TMAO and urea (360 mM urea and 180 mM TMAO). *$p<0.05$ vs. control. Further details regarding methodology are provided in Example 2.
Figure 4:
FIG. 4 is a series of images of histological samples at day 28 for control (left) and 55 mM TMAO group stained with Picosirius Red for collagen. Bar=1 mm. Further details regarding methodology are provided in Example 2.

The normalized GAG and collagen content in the 55 mM TMAO group were significantly greater than control at day 28 (see e.g., FIG. 3), and histology showed an even distribution of GAG and collagen throughout the thickness of the construct (see e.g., FIG. 4.).

Results also showed that lower concentrations of urea did not have adverse effects on the mechanical or biochemical properties (see e.g., FIG. 2 and FIG. 3). But groups with a high concentration of urea (360 mM) did not increase from day 0. While the addition of TMAO with urea helped to slightly mitigate the effects of the urea on the mechanical and biochemical properties, the properties were significantly lower than the control group (see e.g., FIG. 2 and FIG. 3).

As demonstrated above, as a culture media supplement, TMAO was observed to significantly increase engineered cartilage mechanical and biochemical properties. This is the first study to the Inventors' knowledge, that has demonstrated the beneficial effects of this organic compound, $(CH_3)_3NO$, on cartilaginous tissue development in culture.

Example 3

The following example shows transient application of TMAO (initial 14 days of culture) to the culture media improved mechanical and biochemical properties throughout the culture period. Culture media was supplemented with 0 mM, 5 mM, 50 mM, 100 mM or 200 mM of TMAO for the first 14 days of culture (transient application).

Methods are according to Example 2 unless otherwise indicated. Statistical analysis included a two-way ANOVA (factors: time & concentration) with a Bonferonni post-hoc test.

Results showed that transient application of TMAO (initial 14 days of culture) to the culture media showed improved mechanical and biochemical properties throughout the culture period.

Figure 5:
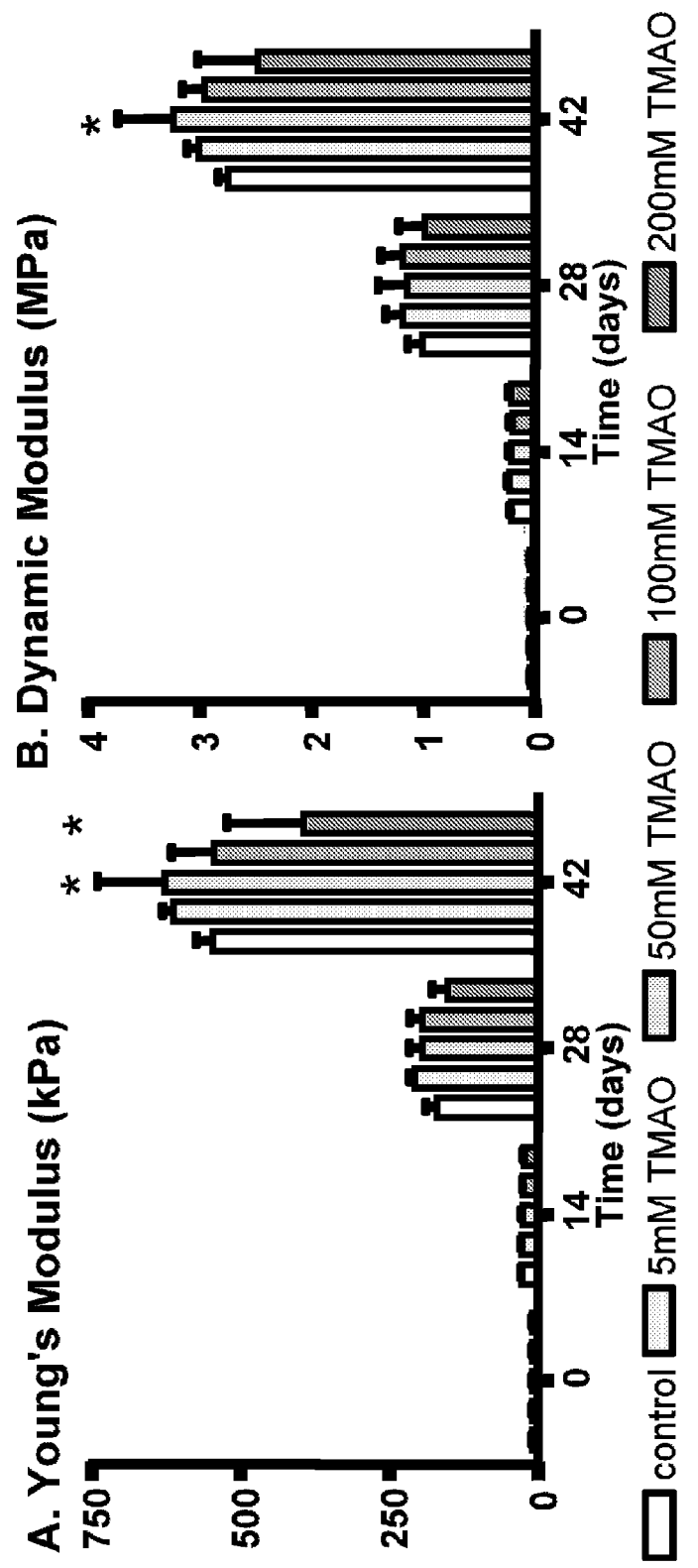
FIG. 5 is a series of bar graphs showing Young's modulus (FIG. 5A) and the dynamic modulus (FIG. 5B) for culture media was supplemented with 0 mM, 5 mM, 50 mM, 100 mM or 200 mM of TMAO for the first 14 days of culture (transient application). * represents $p<0.001$ versus respective day 42 groups, for a two-way ANOVA (factors: time & concentration) with a Bonferroni post-hoc test. Further details regarding methodology are provided in Example 3.

By day 42, the Young's modulus and the dynamic modulus of the 50 mM TMAO group was significantly greater than the control group (see e.g., FIG. 5). This dose dependent study suggests an optimal concentration of TMAO of between about 5 mM and about 100 mM.

Figure 6:
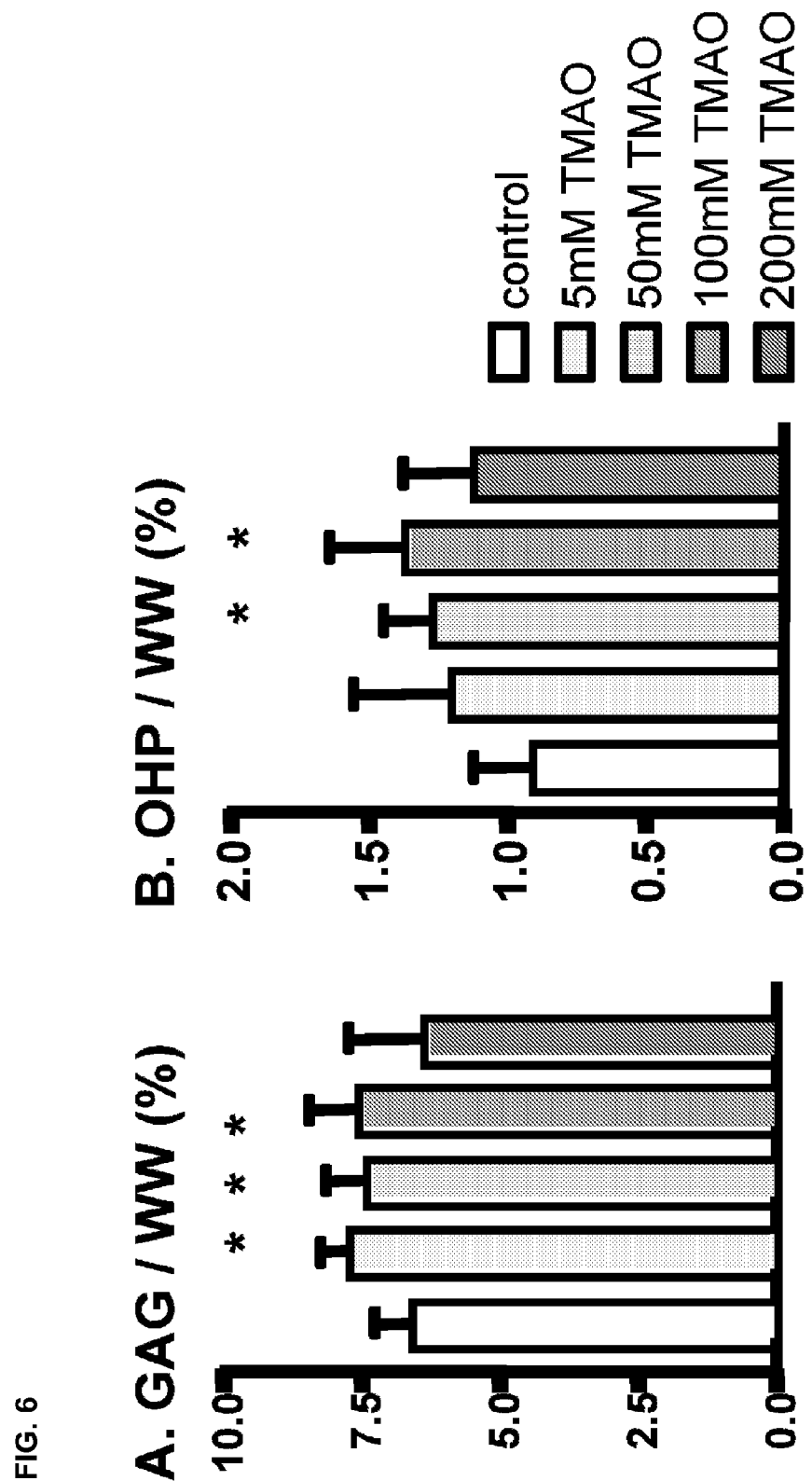
FIG. 6 is a series of bar graphs showing GAG (FIG. 6A) and OHP content (FIG. 6B) with TMAO concentrations of 5 mM, 50 mM and 100 mM.

Results also showed that GAG content (normalized to wet weight at day 42) the TMAO groups with concentrations of 5 mM, 50 mM and 100 mM were up to 17% greater than the control values (see e.g., FIG. 6A). For OHP content (normalized to the wet weight at day 28), TMAO groups were greater than the control, reaching significance for concentrations of 50 mM and 100 mM TMAO (see e.g., FIG. 6B). The 100 mM TMAO group was approximately 50% greater than the control values.

Example 4

The following example shows digestion of mature tissue engineered constructs (i.e., at day 14) with chondroitinase (chABC) temporarily suppresses the GAG content, increases the collagen content and improves the mechanical properties.

Methods are according to Example 2 unless otherwise indicated.

Mature constructs were enzymatically digested for 48 hours at day 14 with 0.15 U/mL of chondroitinase ABC (chABC), which degrades proteoglycans, then cultured with CM or CM supplemented with 5 mM of TMAO. Digestion of mature tissue engineered constructs with chondroitinase (cABC) temporarily suppresses the glycosaminoglycan (GAG) content, increases the collagen content and improves the mechanical properties (see Bian et al. 2009 Tissue Eng Part A 15(8), 2065-2072). Following the digestion, constructs were cultured in either CM or CM supplemented with 5 mM TMAO. A Student's t-test was performed to compare properties of the constructs cultured in CM or CM supplemented with TMAO. Significance was set at $\alpha$=0.05.

Results showed that digestion of tissue engineered constructs with cABC decreased the EY from 94.3±7.1 kPa at day 14 to 15±1.3 kPa.

Figure 7:
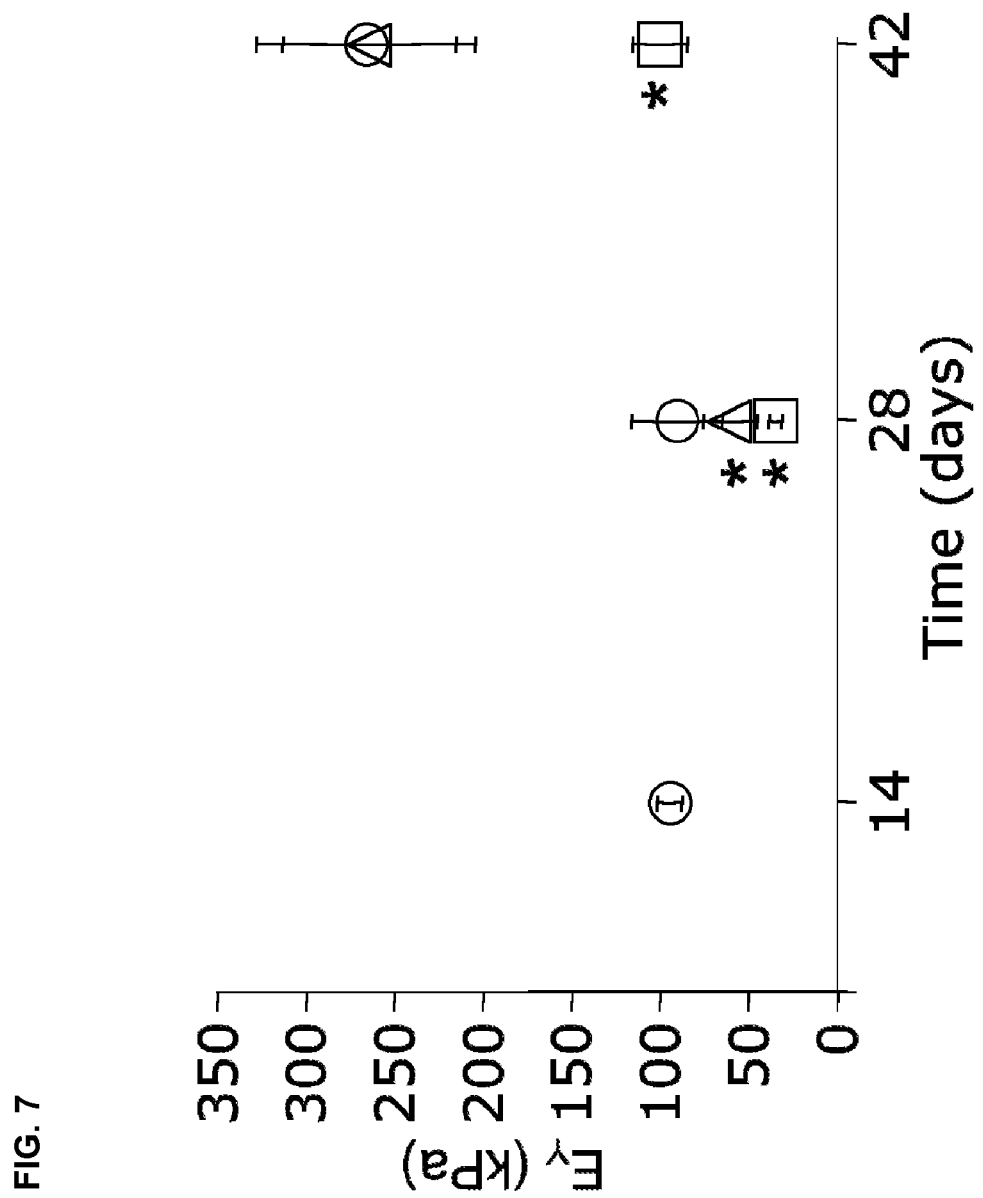
FIG. 7 is a scatter plot showing normalized equilibrium modulus $E\gamma$ (kPa) of constructs digested with cABC (squares and triangles) at days 14, 28, and 42. *$p<0.05$ vs. control. Further details regarding methodology are provided in Example 4.

CM media supplemented with TMAO exhibited significantly greater mechanical and biochemical properties relative to CM alone by day 28, which persisted to day 42 (see e.g., FIG. 7). By day 42, the EY reached 115.6±38.1 kPa and 235.6±75.8 kPa for CM and TMAO groups, respectively.

Figure 8:
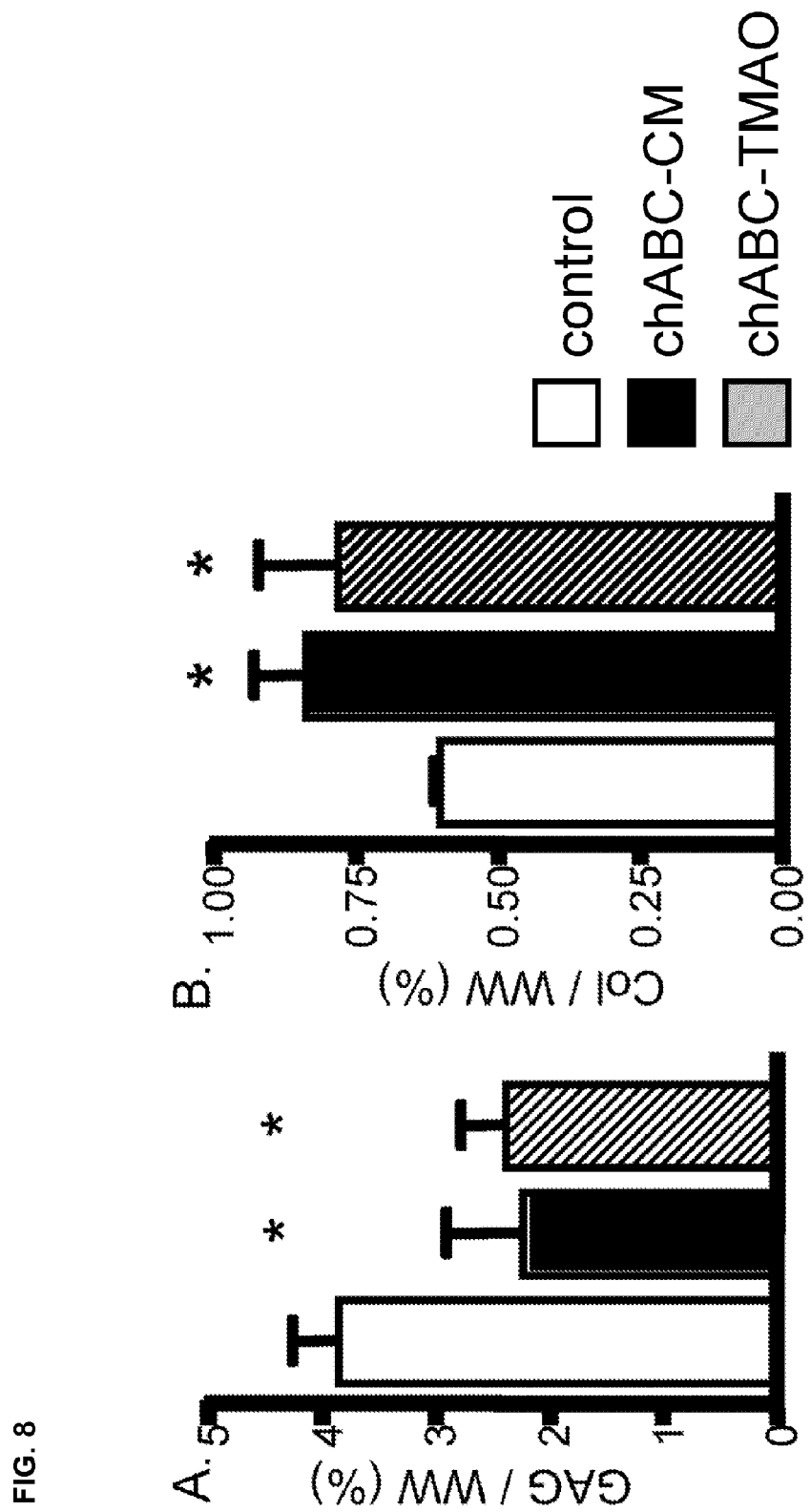
FIG. 8 is a series of bar graphs showing GAG (FIG. 7A) and OHP (FIG. 7B) content normalized to wet weight at day 28 for undigested constructs (white bars), digested constructs cultured with CM (black) or 5 mM TMAO (diagonal stripes). Further details regarding methodology are provided in Example 4.

Results further showed the collagen content of the digested samples was 30% greater than the undigested engineered cartilage (see e.g., FIG. 8).

As shown above, supplementing the culture media with TMAO following the chABC digestion results in a quicker recovery of the mechanical properties and increases the collagen content compared to the control. Thus, TMAO in combination with controlled cABC enzymatic treatment can therefore provide a strategy to increase collagen content towards native cartilage levels.

Example 5

The following example shows effects of TMAO are in nucleus pulposus (spine tissue).

Methods are according to Example 2 unless otherwise indicated.

Micropellets (scaffold-free constructs comprised of aggregated cells only) consisting of nucleus pulposus (spine tissue) cells were cultured for 28 days. The media was supplement with either 5 mM or 50 mM TMAO. Micropellets cultured in CM were used as the control. Micropellets were cultured for 6 weeks and analyzed for biochemistry (i.e. GAG, DNA and OHP contents).

Figure 9:
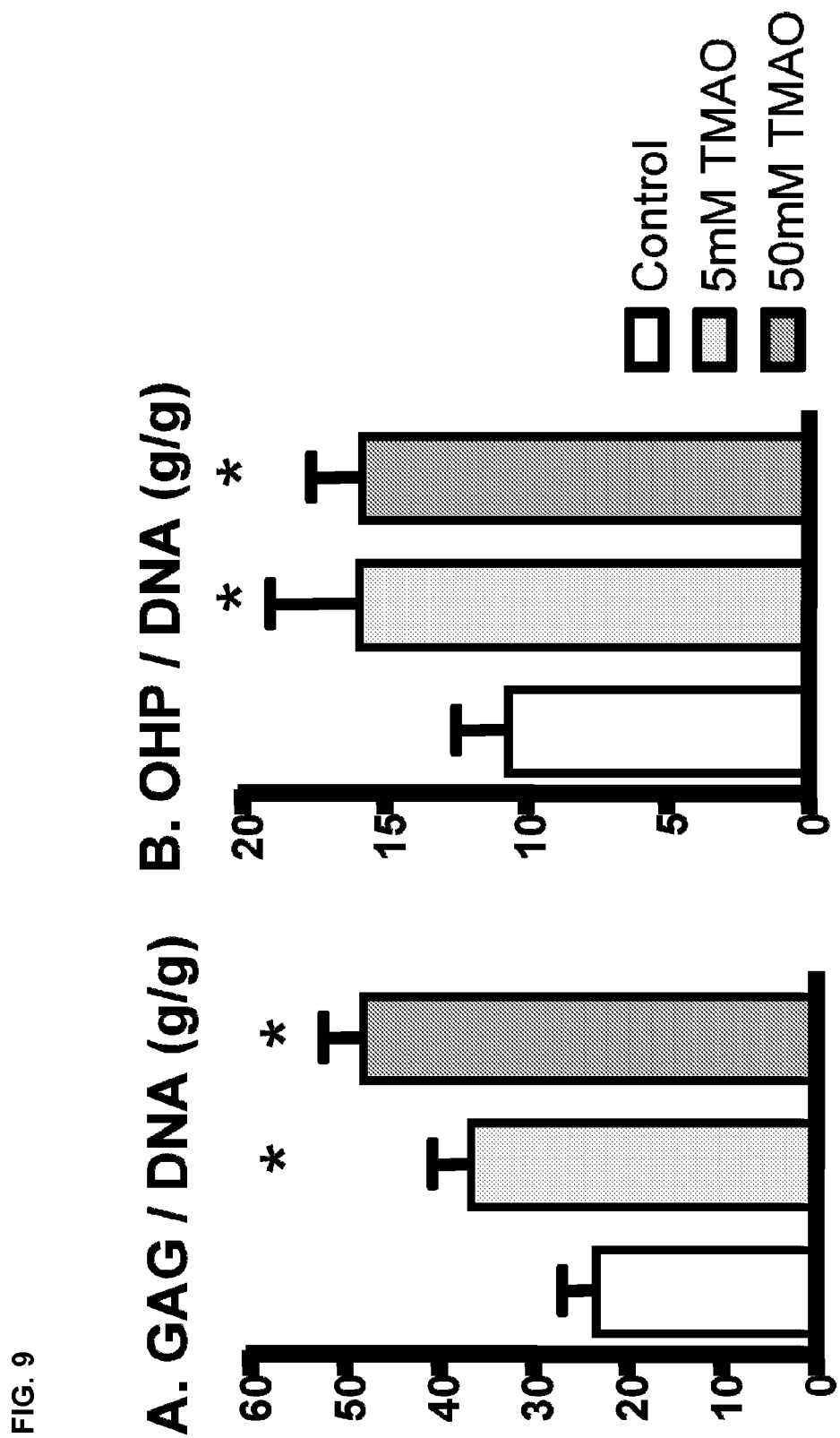
FIG. 9 is a series of bar graphs showing GAG (FIG. 9A) and OHP (collagen) (FIG. 9B) content normalized by DNA content at day 42 of nucleus pulposus (spine tissue) cells cultured in a media supplemented with either 5 mM or 50 mM TMAO. Further details regarding methodology are provided in Example 5.

Results showed there was a graded effect of the TMAO concentration with the GAG production of the micropellets (see e.g., FIG. 9A). Micropellets cultured in CM supplemented with TMAO had a 50% increase in collagen production (see e.g., FIG. 9B).

The invention claimed is:

1. A method for producing cartilage tissue, comprising:
   (a) introducing chondrogenic progenitor cells into a scaffold comprising a matrix material;
   (b)(i) contacting the chondrogenic progenitor cells with chondroitinase (cABC) and culturing the chondrogenic progenitor cells in a culture medium comprising trimethylamine N-oxide (TMAO) or (ii) culturing the chondrogenic progenitor cells in a culture medium comprising trimethylamine N-oxide (TMAO) and cABC;
   (c) differentiating the cultured chondrogenic progenitor cells into connective tissue cells;
   (d) digesting the cultured chondrogenic progenitor cells or connective tissue cells with the cABC; and
   (e) forming cartilage tissue from the connective tissue cells, the cartilage tissue comprising an extracellular matrix, the extracellular matrix comprising collagen fibers, proteoglycans, and elastin fibers;
   wherein,
   the cartilage tissue has a greater elastic modulus than a control engineered cartilage tissue; and
   the cartilage tissue has a greater collagen content than a control engineered cartilage tissue.

2. The method of claim 1, wherein the culture medium comprises at least about 0.01 U/mL, at least about 0.02 U/mL, at least about 0.03 U/mL, at least about 0.04 U/mL, at least about 0.05 U/mL, at least about 0.06 U/mL, at least about 0.07 U/mL, at least about 0.08 U/mL, at least about 0.09 U/mL, at least about 0.10 U/mL, at least about 0.11 U/mL, at least about 0.12 U/mL, at least about 0.13 U/mL, at least about 0.14 U/mL, at least about 0.15 U/mL, at least about 0.16 U/mL, at least about 0.17 U/mL, at least about 0.18 U/mL, at least about 0.19 U/mL, at least about 0.20 U/mL, at least about 0.25 U/mL, at least about 0.30 U/mL, at least about 0.40 U/mL, at least about 0.50 U/mL, at least about 0.60 U/mL, at least about 0.70 U/mL, at least about 0.80 U/mL, at least about 0.90 U/mL, at least about 1.0 U/mL, at least about 1.1 U/mL, at least about 1.2 U/mL, at least about 1.3 U/mL, at least about 1.4 U/mL, or at least about 1.5 U/mL cABC.

3. The method of claim 1, wherein the cultured chondrogenic progenitor cells form a connective tissue.

4. The method of claim 1, wherein the cultured chondrogenic progenitor cells form cartilage tissue having increased stiffness compared to cartilage tissue not cultured in the presence of TMAO.

5. The method of claim 1, comprising:
   introducing a chondrogenic progenitor cell into or onto a biocompatible matrix.

6. The method of claim 1, wherein the culture medium comprises about 10 mM, about 20 mM, about 30 mM, about 40 mM, about 50 mM, about 60 mM, about 70 mM, about 80 mM, about 90 mM, about 100 mM, about 110 mM, about 120 mM, about 130 mM, about 140 mM, about 150 mM, about 160 mM, about 170 mM, about 180 mM, about 190 mM, about 200 mM, about 250 mM, about 300 mM, about 400 mM, about 450 mM, about 500 mM, about 550 mM, about 600 mM, about 650 mM, about 700 mM, about 750 mM, about 800 mM, about 850 mM, about 900 mM, about 950 mM, or about 1,000 mM TMAO.

7. The method of claim 1, wherein the culture medium comprises about 5 mM to about 100 mM TMAO.

8. The method of claim 1, wherein the culture medium further comprises urea.

9. The method of claim 2, wherein the culture medium comprises about 10 mM, about 20 mM, about 30 mM, about 40 mM, about 50 mM, about 60 mM, about 70 mM, about 80 mM, about 90 mM, about 100 mM, about 110 mM, about 120 mM, about 130 mM, about 140 mM, about 150 mM, about 160 mM, about 170 mM, about 180 mM, about 190 mM, about 200 mM, about 250 mM, about 300 mM, about 400 mM, about 450 mM, about 500 mM, about 550 mM, about 600 mM, about 650 mM, about 700 mM, about 750 mM, about 800 mM, about 850 mM, about 900 mM, about 950 mM, or about 1,000 mM urea.

10. The method of claim 2, wherein the culture medium comprises TMAO and urea at a ratio (TMAO:urea) of about 100:1, about 90:1, about 80:1, about 70:1, about 60:1, about 50:1, about 40:1, about 30:1, about 20:1, about 10:1, about 9:1, about 8:1, about 7:1, about 6:1, about 5:1, about 4:1, about 3:1, about 2:1, about 1:1, about 1:2, about 1:3, about 1:4, about 1:5, about 1:6, about 1:7, about 1:8, about 1:9, about 1:10, about 1:20, about 1:30, about 1:40, about 1:50, about 1:60, about 1:70, about 1:80, about 1:90, or about 1:100.

11. The method of claim 1, wherein the culture medium further comprises Dulbecco's Modified Eagle Medium (DMEM).

12. The method of claim 1, wherein the culture medium further comprises one or more of dexamethasone, proline, ascorbate 2-phosphate, sodium pyruvate, insulin, transferrin, sodium selenite, penicillin, streptomycin amphotericin, or TGF-$\beta_3$.

13. The method of claim 1, wherein the chondrogenic progenitor cells comprise mesenchymal stem cells (MSCs), osteochondrogenic MSCs, chondrogenic MSCs, osteoblasts, chondrocytes, hypertrophic chondrocytes, fibroblastic cells, interstitial fibroblasts, tendon fibroblasts, dermal fibroblasts, ligament fibroblasts, periodontal fibroblasts, gingival fibroblasts, craniofacial fibroblasts, colony-forming unit-fibroblasts (CFU-Fs), or hypertrophic chondrocytes.

14. The method of claim 1, wherein the chondrogenic progenitor cells comprise chondrocytes.

15. The method of claim 1, wherein the cartilage tissue comprises hyaline cartilage, elastic cartilage, or fibrocartilage, or a combination thereof.

16. The method of claim 1, wherein the matrix material comprises a synthetic polymer, a naturally occurring polymer or a naturally occurring polymer.

17. The method of claim 16, wherein the matrix material comprises polyethylene glycol, bioerodible polymers, polylactide, polyglycolic acid, polylactide-co-glycolide, polycaprolactone, polyester, poly-L-lactic acid, polyanhydride, polyglactin, polyglycolic acid, polycarbonates, polyamides, polyanhydrides, polyamino acids, polyortho esters, polyacetals, polycyanoacrylates, polyphosphazene, degradable polyurethanes, non-erodible polymers, polyacrylates, ethylene-vinyl acetate polymers, acyl substituted cellulose acetates, acyl substituted cellulose acetate derivatives, non-erodible polyurethanes, polystyrenes, polyvinyl chloride, polyvinyl fluoride, polyvinyl pyrrolidone, polyvinylimidazole, chlorosulphonated polyolefins, polyethylene oxide, polyvinyl alcohol, polyvinyl alcohol sponge, synthetic marine adhesive proteins, Teflon®, nylon, polyethylene oxide-polypropylene glycol block copolymer; polyD,L-lactide-co-glycolide fiber matrix, agarose, alginate, calcium alginate gel, fibrin, fibrinogen, fibronectin, collagen, collagen gel, gelatin, hyaluronic acid, or chitin, or combinations thereof.

18. The method of claim 16, where the matrix material comprises agarose hydrogel.

* * * * *